(12) United States Patent
Du

(10) Patent No.: US 12,255,478 B2
(45) Date of Patent: Mar. 18, 2025

(54) HAND WARMER CHARGING CASE AND HANDWARMER KIT

(71) Applicant: Yanan Du, Shenzhen (CN)

(72) Inventor: Yanan Du, Shenzhen (CN)

(73) Assignee: Shenzhen Tianman Technology Co., Ltd., Shenzhen (CN)

( * ) Notice: Subject to any disclaimer, the term of this patent is extended or adjusted under 35 U.S.C. 154(b) by 0 days.

(21) Appl. No.: 18/887,055

(22) Filed: Sep. 17, 2024

(65) Prior Publication Data

US 2025/0015618 A1 Jan. 9, 2025

(51) Int. Cl.
| | |
|---|---|
| H01M 10/46 | (2006.01) |
| A61F 7/00 | (2006.01) |
| H02J 7/00 | (2006.01) |
| H02J 7/34 | (2006.01) |

(52) U.S. Cl.
CPC ............... *H02J 7/0044* (2013.01); *A61F 7/00* (2013.01); *H02J 7/342* (2020.01); *A61F 2007/0036* (2013.01)

(58) Field of Classification Search
CPC ........ H02J 7/0044; H02J 7/0042; H02J 7/342; A61F 2007/0036; A61F 7/00
USPC .......................................... 320/107, 114, 115
See application file for complete search history.

(56) References Cited

U.S. PATENT DOCUMENTS

2019/0076118 A1* 3/2019 Dohm .................... A61F 7/0241

FOREIGN PATENT DOCUMENTS

| CN | 105054525 | A | * | 11/2015 |
| FR | 3110221 | A1 | * | 11/2021 |
| JP | 3221961 | U | * | 7/2019 |

* cited by examiner

Primary Examiner — Edward Tso

(57) ABSTRACT

A hand warmer charging case includes an accommodating housing and an accommodating cover. The accommodating housing is provided with a storage space for storing a target hand warmer. The accommodating housing is further provided with an accommodating space. The accommodating space is configured to accommodate a rechargeable power supply and a circuit board matched with the rechargeable power supply. The accommodating cover is movably connected to the accommodating housing in a movable manner, and is configured to close or open the storage space. During use, the accommodating cover that cooperates with the accommodating housing is opened to opening the storage space provided in the accommodating housing. A power bank hand warmer that needs to be charged or is temporarily in idle is put into the storage space, and the accommodating cover that cooperates with the accommodating housing is closed, thereby closing the storage space provided in the accommodating housing.

19 Claims, 8 Drawing Sheets

HAND WARMER CHARGING CASE AND HANDWARMER KIT

TECHNICAL FIELD

The present disclosure relates to the technical field of charging cases, and in particular to, a hand warmer charging case.

BACKGROUND OF THE INVENTION

With the improvement of the living standard, consumers have increasingly high requirements for the battery life, maintenance, and cleanliness of hand warmers. For example, consumers desire that a power bank hand warmer has a good warming effect and is portable, and put forward higher requirements for the battery life, maintenance, and cleanliness of the power bank hand warmer.

The existing power bank hand warmers on the market, either one-piece or split type, can be usually charged through a charging cable only. Therefore, the battery life during movement is relatively short. Moreover, when being charged or in idle, the power bank hand warmer is easily contaminated by contaminants such as fallen dust and accidentally spilled coffee. Therefore, there is an urgent need on the market to provide charging equipment that can maintain a hand warmer during charging or idling and avoid contamination with the fallen dust, the accidentally spilled coffee, and other contaminants, and is portable.

Therefore, the present disclosure provides a hand warmer charging case that can effectively solve the above-mentioned problems.

SUMMARY OF THE INVENTION

To overcome the shortcomings in the prior art, the present disclosure provides a hand warmer charging case which has a simple structure, can maintain a power bank hand warmer, thereby avoiding the problem below: When being charged or in idle, the power bank hand warmer is easily contaminated by fallen dust, accidentally spilled coffee, and other contaminants, and is portable.

The technical solution adopted by the present disclosure to solve the technical problem is as follows.

A hand warmer charging case includes:
an accommodating housing, wherein the accommodating housing is provided with a storage space for storing a target hand warmer; the accommodating housing is further provided with an accommodating space; the accommodating space is configured to accommodate a rechargeable power supply and a circuit board matched with the rechargeable power supply; and
an accommodating cover, wherein the accommodating cover is movably connected to the accommodating housing in a movable manner, and is configured to close or open the storage space.

As an improvement of the present disclosure, the accommodating housing includes an inner housing and an outer housing; the storage space is provided on the inner housing; the outer housing is coupled with the inner housing; and the accommodating space is defined jointly by the outer housing and the inner housing.

As an improvement of the present disclosure, the inner housing is provided with a storage shell for defining the storage space; the storage shell is provided with a storage opening communicated to the storage space; the accommodating cover includes an inner cover and an outer cover; the inner cover is provided with a storage chamber and an opening communicated to the storage chamber; and the opening corresponds to the storage opening.

As an improvement of the present disclosure, the inner housing is provided with a positioning boss; the positioning boss is in a similarly trapezoid shape with a narrow top and a wide bottom; the inner cover is provided with a positioning chamber and a positioning opening communicated to the positioning chamber; and the positioning opening corresponds to the positioning boss.

As an improvement of the present disclosure, the hand warmer charging case further includes a connecting shaft, the accommodating housing and the accommodating cover are movably connected through the connecting shaft to enable the accommodating cover to close or open the storage space.

As an improvement of the present disclosure, the inner housing is provided with a connecting boss; the outer cover is provided with a connecting groove corresponding to the connecting boss; and the connecting boss and the connecting groove are movably connected through the connecting shaft.

As an improvement of the present disclosure, the connecting boss is provided with a connecting hole; connecting clamping slots are provided in two ends of the connecting groove; the connecting shaft passes through the connecting hole of the connecting boss and is clamped with the connecting clamping slots provided in the two ends of the connecting groove.

As an improvement of the present disclosure, the inner housing is provided with a first butting part; the inner cover is provided with a second butting part; and when the accommodating cover closes the storage space, the first butting part is butted to the second butting part.

As an improvement of the present disclosure, a first magnetic suction element is arranged below the first butting part, and a second magnetic suction element is arranged above the second butting part; and when the first butting part is butted to the second butting part, attraction force exists between the first magnetic suction element and the second magnetic suction element.

As an improvement of the present disclosure, the inner housing is further provided with a power supply positioning shell; and the power supply positioning shell is fixedly connected to the storage shell; and the power supply positioning shell is configured to position and fix the rechargeable power supply.

As an improvement of the present disclosure, the inner housing is further provided with a first mounting part; the outer housing is provided with a second mounting part; and the first mounting part is detachably connected to the second mounting part.

As an improvement of the present disclosure, the first mounting part is provided with a convex positioning strip; the second mounting part is provided with a positioning groove; and when the first mounting part is connected to the second mounting part, the convex positioning strip cooperates with the positioning groove for positioning to avoid misalignment during the connection between the inner housing and the outer housing.

As an improvement of the present disclosure, the first mounting part is provided with a convex clamping strip; the second mounting part is provided with a convex clamping block; and when the first mounting part is connected to the second mounting part, the convex clamping strip is matched and clamped with the convex clamping block, so that the inner housing and the outer housing are connected by clamping.

As an improvement of the present disclosure, the convex positioning strip is arranged around the convex clamping strip in a spacing manner; the convex clamping strip is provided with a clamping strip hole; and a position of the clamping strip hole is correspondingly spaced apart from the convex positioning strip.

As an improvement of the present disclosure, the positioning groove is continuously provided around the convex clamping block; and a position of the convex clamping block is matched with the position of the clamping strip hole.

As an improvement of the present disclosure, the storage shell is provided with a clamping protrusion matched with the target hand warmer; and the clamping protrusion enables the storage shell to lock the target hand warmer.

As an improvement of the present disclosure, the target hand warmer includes two hand warmer units; and the two hand warmer units are connected by magnetic suction or a buckle.

As an improvement of the present disclosure, the target hand warmer is integrally formed.

As an improvement of the present disclosure, the circuit board is provided with a charging circuit matched with the rechargeable power supply and a charging port connected to an external power supply.

As an improvement of the present disclosure, the circuit board is provided with a discharging circuit and a discharging port which are matched with the target hand warmer.

Beneficial effects: By the arrangement of the above structure, during use, the accommodating cover that cooperates with the accommodating housing is opened to opening the storage space provided in the accommodating housing. A power bank hand warmer that needs to be charged or is temporarily in idle is put into the storage space, and the accommodating cover that cooperates with the accommodating housing is closed, thereby closing the storage space provided in the accommodating housing. The closed storage space can achieve a good closing effect, avoiding the contamination, caused by fallen dust, accidentally spilled coffee, and other contaminants. To the power bank hand warmer that needs to be charged or is temporarily in idle, greatly improving the maintenance efficiency of the power bank hand warmer that needs to be charged or is temporarily in idle, and enhancing the user experience. The accommodating housing is further provided with the accommodating space. During use, the rechargeable power supply in the storage space charges the power bank hand warmer through the circuit board matched with the rechargeable power supply, the discharging circuit and discharging port which are matched with the target hand warmer. This keeps a surface of the target hand warmer clean while charging a built-in power supply of the target hand warmer, thereby avoiding low battery of the built-in power supply of the target hand warmer and further enhancing the user experience.

BRIEF DESCRIPTION OF DRAWINGS

In order to explain the technical solutions of the embodiments of the present disclosure more clearly, the following will briefly introduce the accompanying drawings used in the embodiments. The drawings in the following description are only some embodiments of the present disclosure. Those of ordinary skill in the art can obtain other drawings based on these drawings without creative work. In addition, the accompanying drawings are not drawn to a scale of 1:1, and the relative dimensions of the various elements are only shown as examples in the diagrams, not necessarily drawn to a true scale.

The present disclosure is further described below in detail in combination with the accompanying drawings and embodiments.

DETAILED DESCRIPTION OF THE INVENTION

Figure 1:
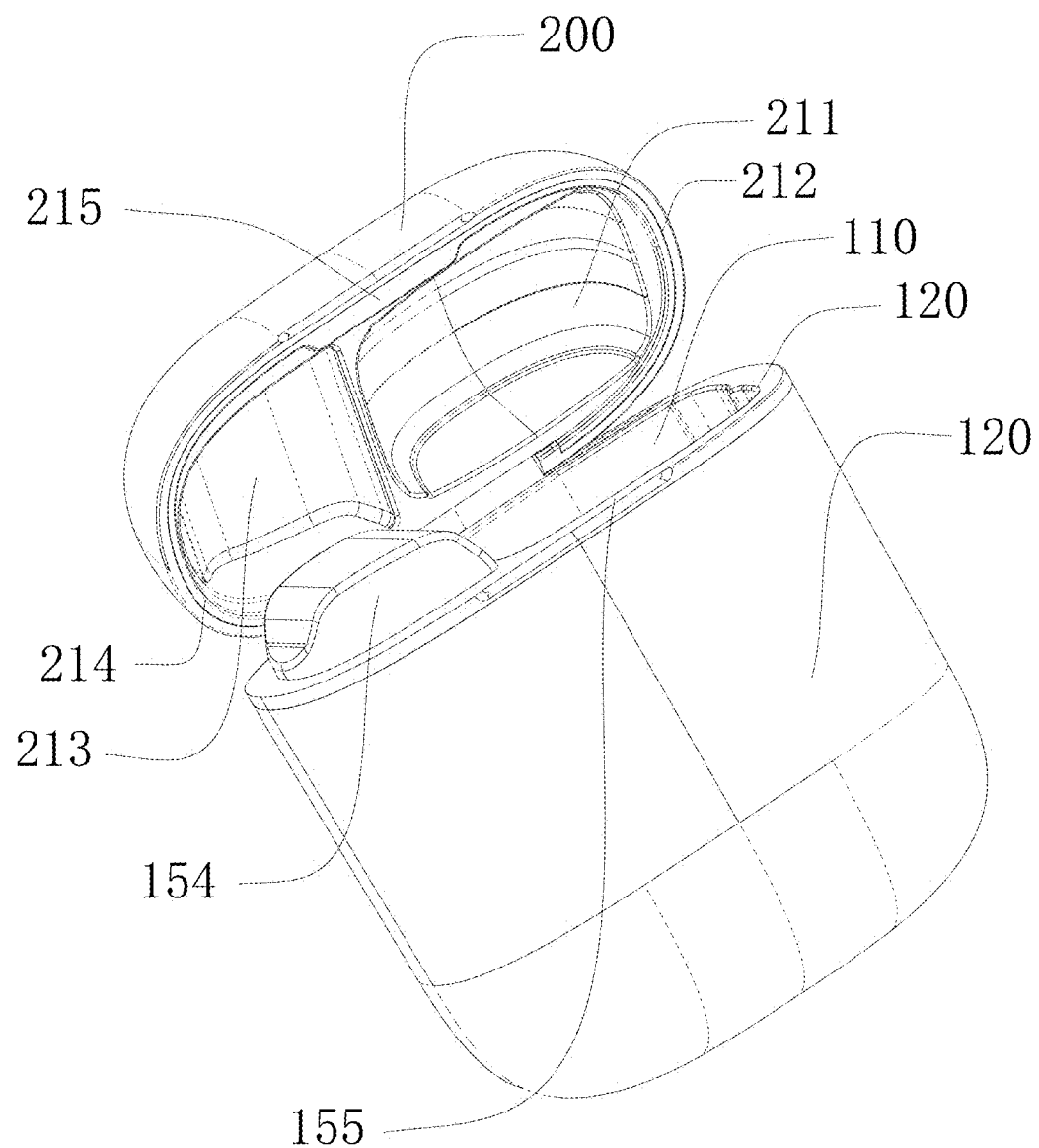
FIG. 1 is a schematic diagram of an entire structure of a hand warmer charging case according to the present disclosure.

To make the aforementioned objectives, features, and advantages of the present disclosure more comprehensible, specific implementations of the present disclosure are described in detail below in conjunction with the accompanying drawings. In the following description, numerous specific details are set forth to provide a thorough understanding of the present disclosure. The present disclosure may, however, be embodied in many forms different from that described here. A person skilled in the art can make similar improvements without departing from the connotation of the present disclosure. Therefore, the present disclosure is not limited by the specific embodiments disclosed below.

In the description of the present disclosure, It is to be understood that, The terms "center", "longitudinal", "transverse", "upper", "lower", "front", "rear", "left", "right", "vertical", "horizontal", "top", "bottom", "inner", "outer", "clockwise", "counterclockwise", and the like indicate azimuth or positional relationships based on the azimuth or positional relationships shown in the drawings, For purposes of convenience only of describing the present disclosure and simplifying the description, Rather than indicating or implying that the indicated device or element must have a particular orientation, be constructed and operated in a particular orientation, therefore, not to be construed as limiting the present disclosure.

In addition, The terms "first" and "second" are used for descriptive purposes only, While not to be construed as indicating or implying relative importance or implicitly specifying the number of technical features indicated thereby, features defining "first," "second," and "second" may explicitly or implicitly include one or more of the described features. In the description of the present disclosure, "multiple" means two or more unless explicitly specified otherwise.

In the description of the present disclosure, it is to be noted that unless otherwise expressly specified and defined, the terms "mounted", "connected", and "connected" are to be construed broadly, for example, as either a fixed connection, or a detachable connection, or an integral connection, either a mechanical connection, or an electrical connection. The specific meaning of the above term in the present disclosure will be understood by those of ordinary skill in the art depending on the particular circumstances, either directly or indirectly via an intermediate medium, communication between the two elements, or interaction between the two elements. The specific meanings of these terms in the present disclosure will be understood by those of ordinary skill in the art as the case may be.

In the present disclosure, unless specific regulation and limitation otherwise, the first feature "onto" or "under" the second feature may include the direct contact of the first feature and the second feature, or may include the contact of the first feature and the second feature through other features between them instead of direct contact. Moreover, the first feature "onto", "above" and "on" the second feature includes that the first feature is right above and obliquely above the second feature, or merely indicates that the horizontal height of the first feature is higher than the second feature. The first feature "under", "below" and "down" the second feature includes that the first feature is right above and obliquely above the second feature, or merely indicates that the horizontal height of the first feature is less than the second feature.

It should be noted that when an element is referred to as being "fixed to" another element, the element can be directly on another component or there can be a centered element. When an element is considered to be "connected" to another element, the element can be directly connected to another element or there may be a centered element. The terms "inner", "outer", "left", "right", and similar expressions used herein are for illustrative purposes only and do not necessarily represent the only implementation.

Figure 2:
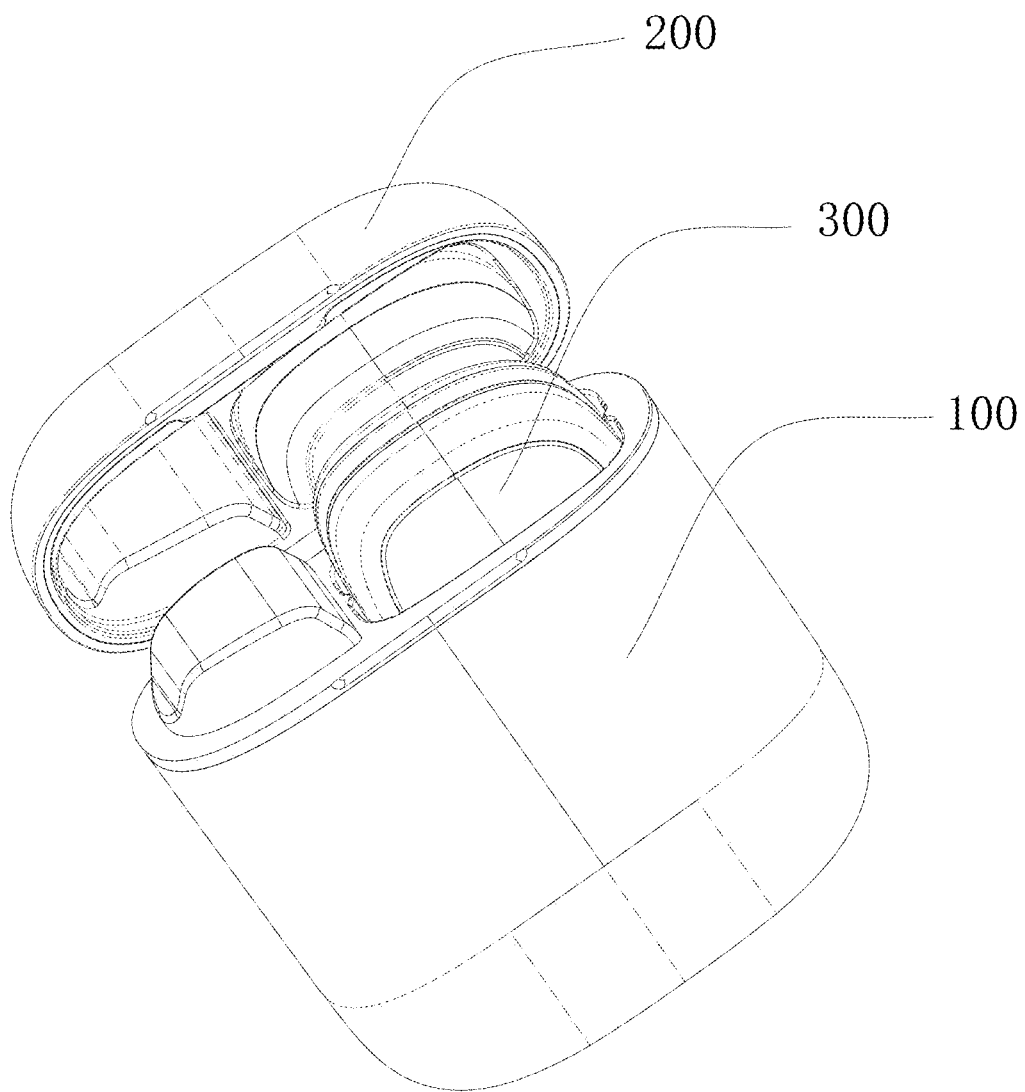
FIG. 2 is a schematic diagram of an entire structure of a hand warmer charging case according to the present disclosure, after a target hand warmer is mounted.
Figure 3:
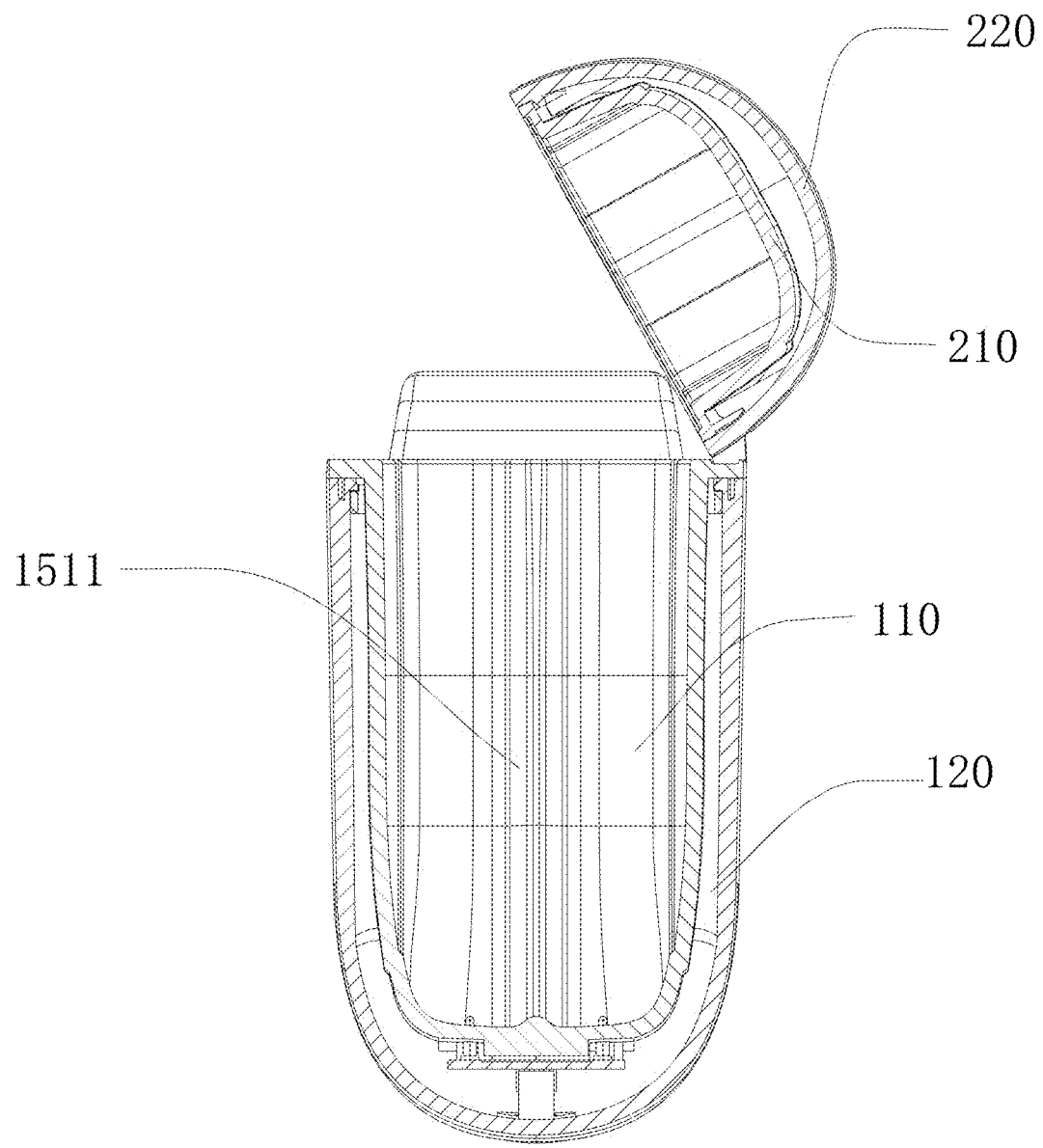
FIG. 3 is a schematic diagram of a first cross-sectional structure of FIG. 1.
Figure 4:
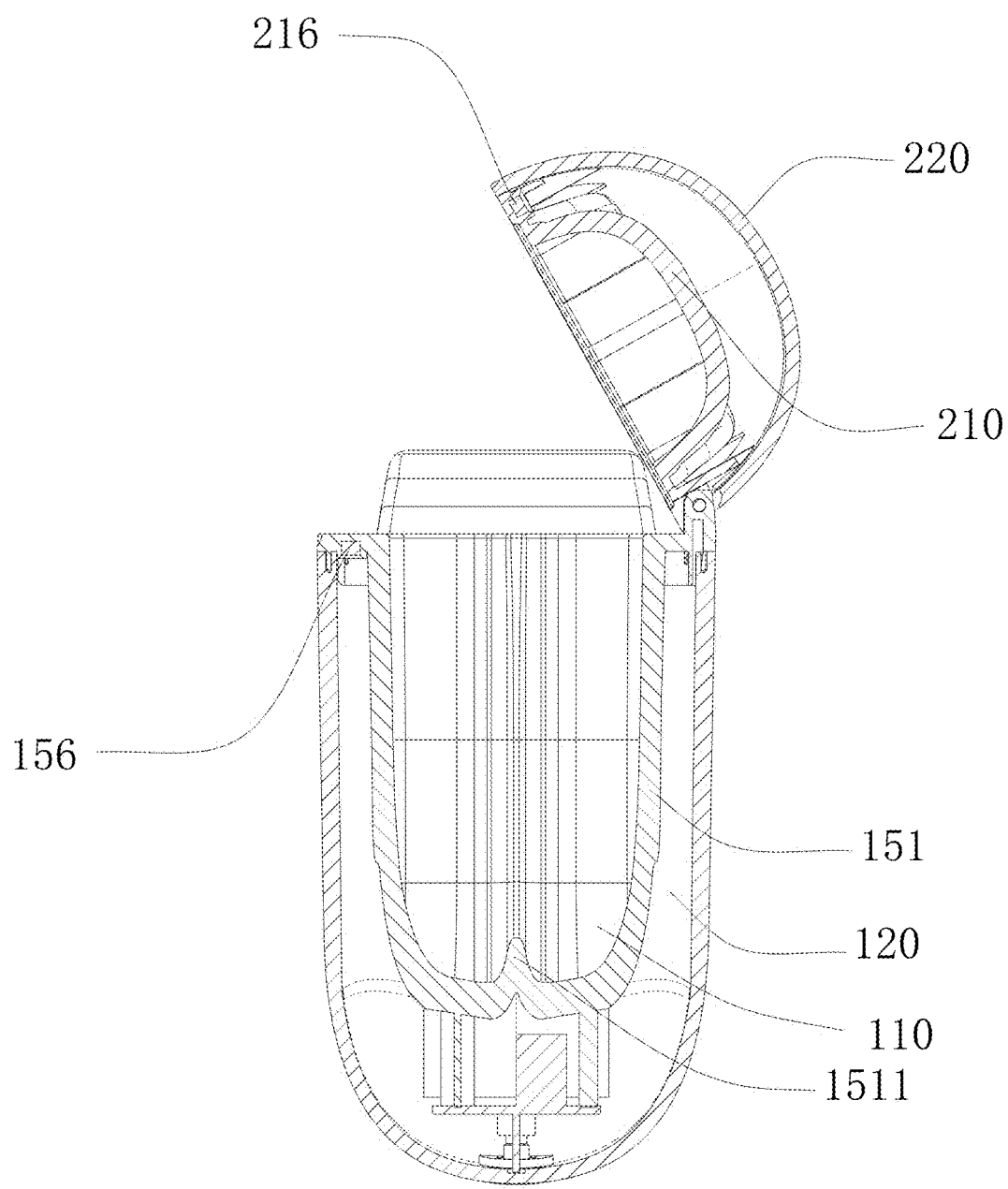
FIG. 4 is a schematic diagram of a second cross-sectional structure of FIG. 1.
Figure 5:
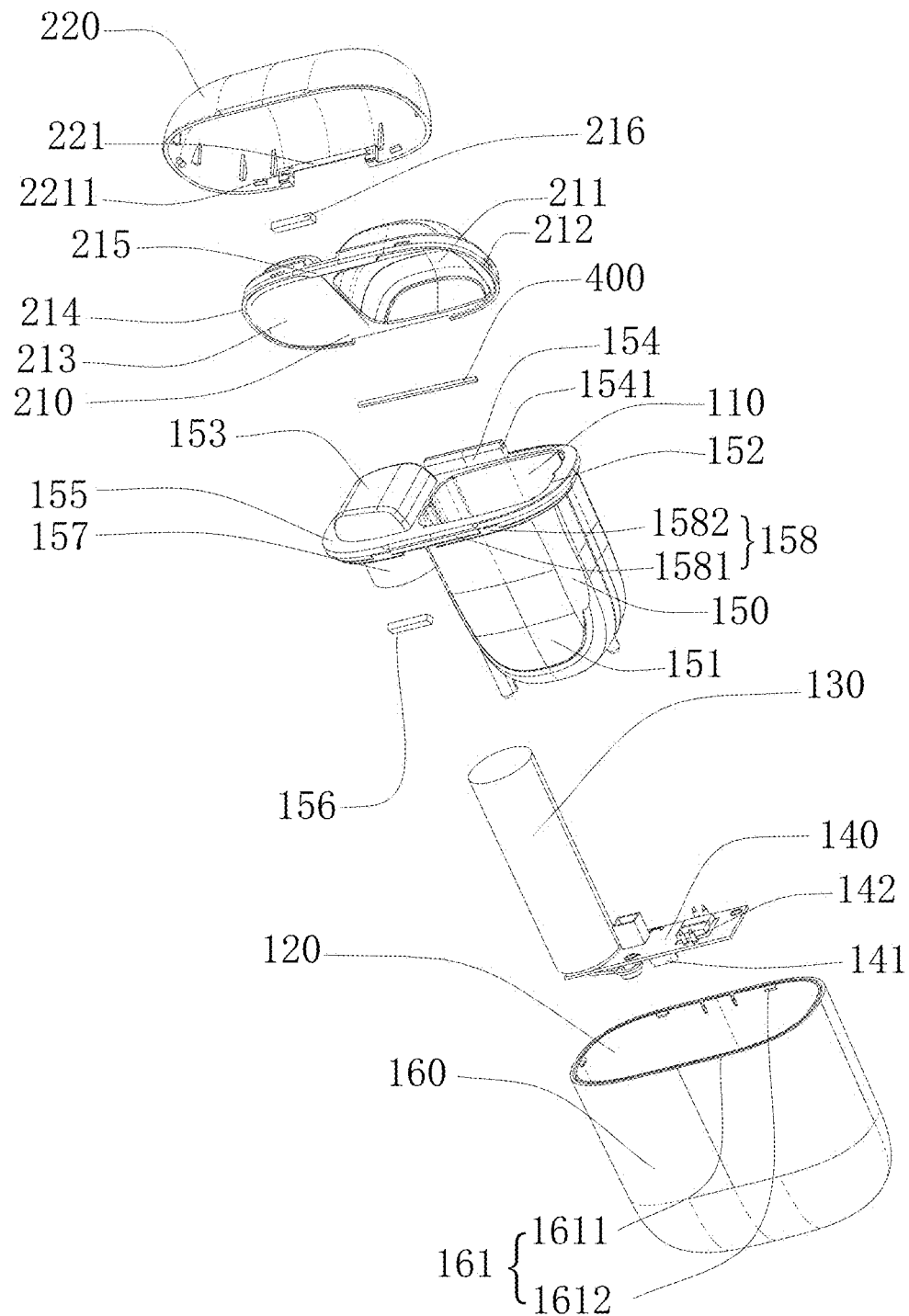
FIG. 5 is a schematic diagram of an exploded structure of FIG. 1.
Figure 6:
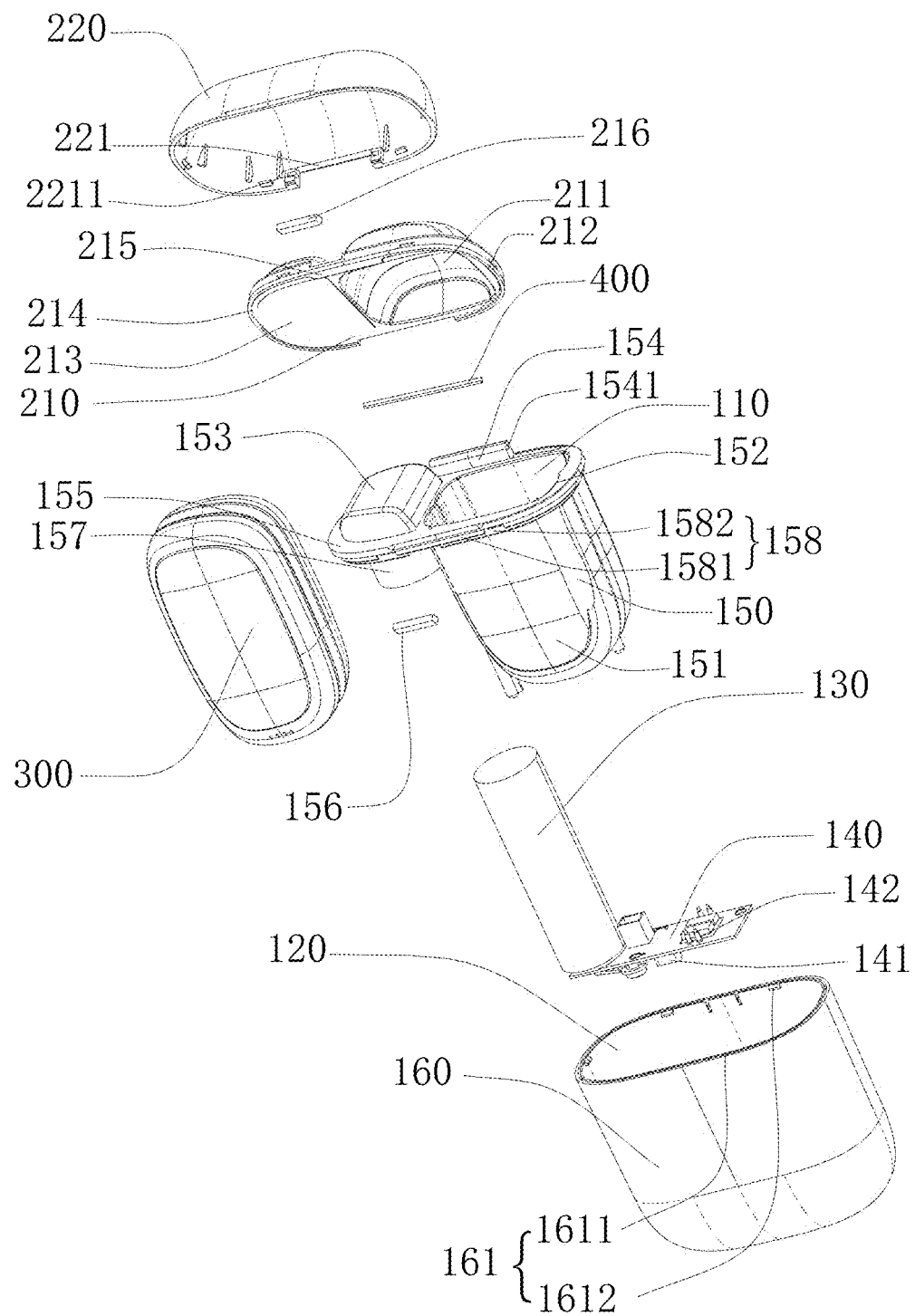
FIG. 6 is a schematic diagram of an exploded structure of FIG. 2.
Figure 7:
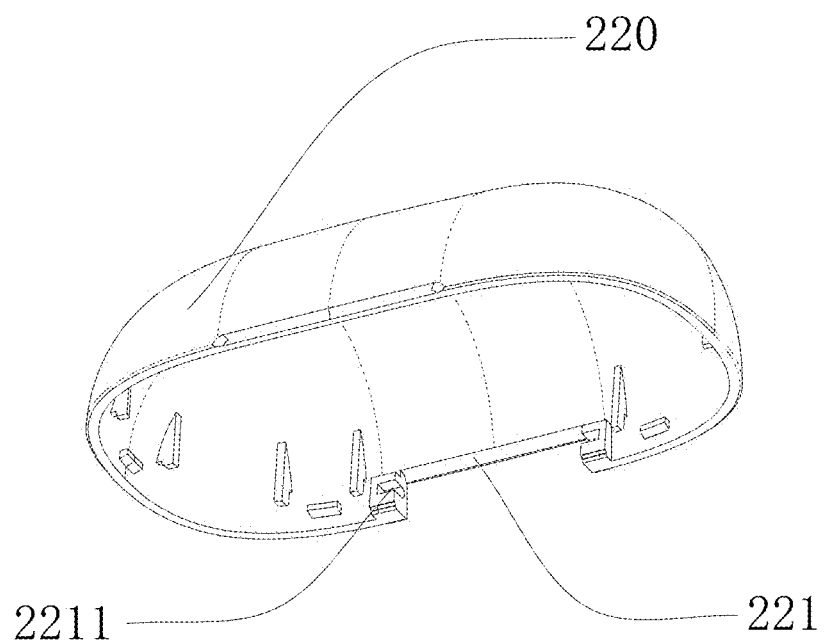
FIG. 7 is an enlarged diagram of an outer cover 220 according to the present disclosure.
Figure 8:
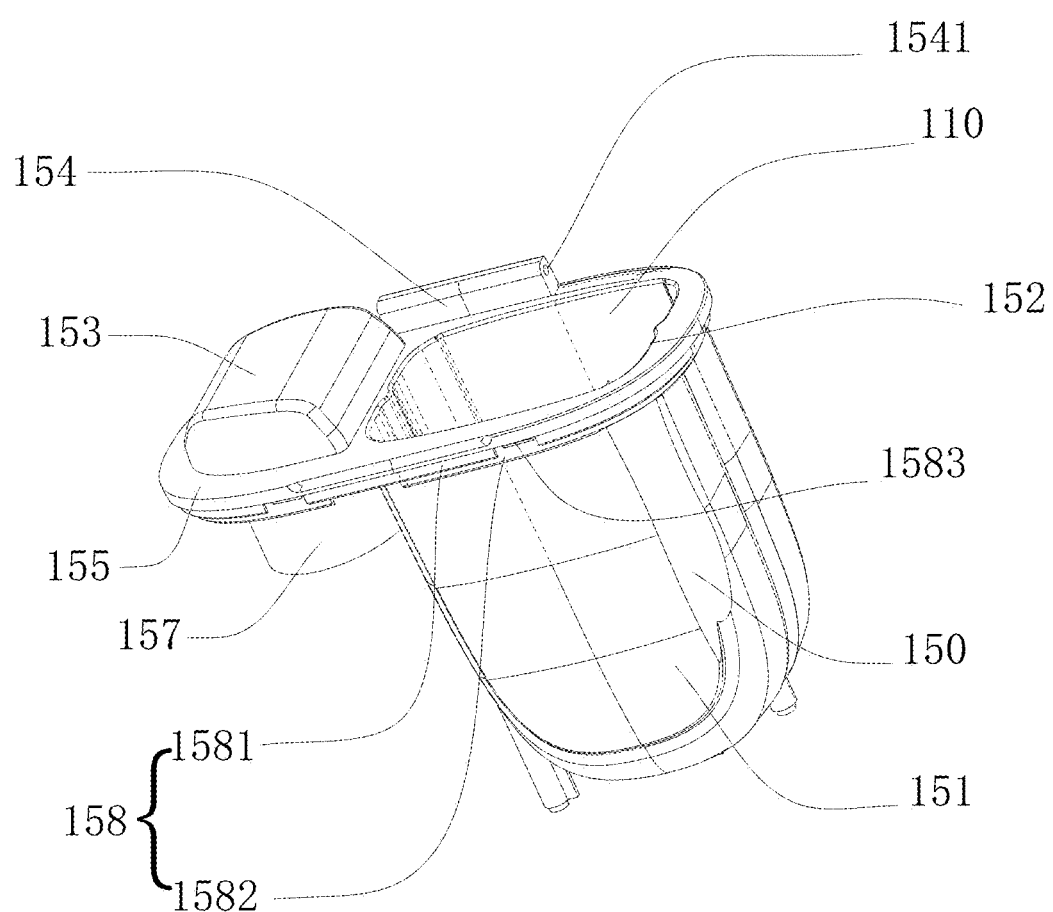
FIG. 8 is an enlarged diagram of an inner housing 150 according to the present disclosure.

Referring to FIG. 1 to FIG. 8, a hand warmer charging case includes:

an accommodating housing 100, wherein the accommodating housing 100 is provided with a storage space 110 for storing a target hand warmer 300; the accommodating housing 100 is further provided with an accommodating space 120; the accommodating space 120 is configured to accommodate a rechargeable power supply 130 and a circuit board 140 matched with the rechargeable power supply 130; and an accommodating cover 200, wherein the accommodating cover 200 is movably connected to the accommodating housing 100 in a movable manner, and is configured to close or open the storage space 110.

The circuit board 140 is provided with a discharging circuit and a discharging port 142 which are matched with the target hand warmer 300.

By the arrangement of the above structure, during use, the accommodating cover 200 that cooperates with the accommodating housing 100 is opened to opening the storage space 110 provided in the accommodating housing 100. A power bank hand warmer that needs to be charged or is temporarily in idle is put into the storage space 110, and the accommodating cover 200 that cooperates with the accommodating housing 100 is closed, thereby closing the storage space 110 provided in the accommodating housing 100. The closed storage space 110 can achieve a good closing effect, avoiding the contamination, caused by fallen dust, accidentally spilled coffee, and other contaminants. To the power bank hand warmer that needs to be charged or is temporarily in idle, greatly improving the maintenance efficiency of the power bank hand warmer that needs to be charged or is temporarily in idle, and enhancing the user experience. The accommodating housing 100 is further provided with the accommodating space 120. During use, the rechargeable power supply 130 in the storage space 120 charges the power bank hand warmer through the circuit board 140 matched with the rechargeable power supply, the discharging circuit and discharging port 142 which are matched with the target hand warmer. This keeps a surface of the target hand warmer clean while charging a built-in power supply of the target hand warmer, thereby avoiding low battery of the built-in power supply of the target hand warmer and further enhancing the user experience.

In this embodiment, the accommodating housing 100 includes an inner housing 150 and an outer housing 160; the storage space 110 is provided on the inner housing 150; the outer housing 160 is coupled with the inner housing 150; and the accommodating space 120 is defined jointly by the outer housing 160 and the inner housing 150. By the arrangement of the above structure, during use, the inner housing 150 defines the storage space 110 alone, and the storage space 110 is only configured to store the target hand warmer, avoiding the risk of contamination by stains on surfaces of other storage objects and further enhancing the cleanliness maintenance effect on a surface of the stored target hand warmer. The outer housing 160 and the inner housing 150 jointly define the accommodating space 120, and the accommodating space 120 is configured to accommodate necessary components for charging and discharging, such as the rechargeable power supply 130 and the circuit board 140. This avoids exposure of these components, prolongs the service lives of the necessary components for charging and discharging, such as the rechargeable power supply 130 and the circuit board 140, and further enhances the user experience.

In this embodiment, the inner housing 150 is provided with a storage shell 151 for defining the storage space 110; the storage shell 151 is provided with a storage opening 152 communicated to the storage space 110; the accommodating cover 200 includes an inner cover 210 and an outer cover 220; the inner cover 210 is provided with a storage chamber 211 and an opening 212 communicated to the storage chamber 211; and the opening 212 corresponds to the storage opening 152. By the arrangement of the above structure, during use, the opening 212 of the storage chamber 211 corresponds to the storage opening 152 of the storage shell 151. When the accommodating cover 200 covers the storage space 110, the opening 212 and the storage opening 152 abut against each other oppositely. The storage shell 151 and the inner cover 210 are completely covered around the target hand warmer 300 together, which avoids the risk of contamination by stains on surfaces of other objects to the maximum extent and achieves a good maintenance and cleaning effects.

In this embodiment, the inner housing 150 is provided with a positioning boss 153; the positioning boss 153 is in a similarly trapezoid shape with a narrow top and a wide bottom; the inner cover 210 is provided with a positioning chamber 213 and a positioning opening 214 communicated to the positioning chamber 213; and the positioning opening 214 corresponds to the positioning boss 153. By the arrangement of the above structure, the positioning boss 153 can be smoothly clamped into the positioning chamber 213 through the positioning opening 214 during use, thereby avoiding misalignment when the accommodating housing 100 is closed with the accommodating cover 200, achieving a better closing effect, and further enhancing the user experience.

In this embodiment, the hand warmer charging case further includes a connecting shaft 400. The accommodating housing 100 and the accommodating cover 200 are movably connected through the connecting shaft 400 to enable the accommodating cover 200 to close or open the storage space 110. By the arrangement of the above structure, during use, the accommodating cover 200 can be rotated relative to the accommodating housing 100 around the connecting shaft 400 used as a rotation center, so as to enable the accommodating cover 200 to close or open the storage space 110, thereby completing the closure or opening of the target hand warmer. It is convenient to use.

In this embodiment, the inner housing 150 is provided with a connecting boss 154; the outer cover 220 is provided with a connecting groove 221 corresponding to the connecting boss 154; and the connecting boss 154 and the connecting groove 221 are movably connected through the connecting shaft 400. The connecting boss 154 is provided with a connecting hole 1541; connecting clamping slots 2211 are provided in two ends of the connecting groove 221; the connecting shaft 400 passes through the connecting hole 1541 of the connecting boss 154 and is clamped with the connecting clamping slots 2211 provided in the two ends of the connecting groove 221. By the arrangement of the above structure, during use, the accommodating cover 200 and the accommodating housing 100 are movably connected, so that the accommodating cover 200 can be rotated relative to the accommodating housing 100 around the connecting shaft 400 used as the rotation center, thereby closing or opening the storage space 110.

In this embodiment, the inner housing 150 is provided with a first butting part 155; the inner cover 210 is provided with a second butting part 215; and when the accommodating cover 200 closes the storage space 110, the first butting part 155 is butted to the second butting part 215. A first magnetic suction element 156 is arranged below the first butting part 155, and a second magnetic suction element 216 is arranged above the second butting part 215; and when the first butting part 155 is butted to the second butting part 215, attraction force exists between the first magnetic suction element 156 and the second magnetic suction element 216. By the arrangement of the above structure, during use, when the storage space 110 is closed, the butting parts are in surface contact. On the one hand, a better closing effect and a larger error-tolerant rate of covering can be achieved. To close the product, even if the inner cover 210 is slightly misaligned, it does not affect the actual closing effect. On the other hand, it is convenient to install the magnetic elements on two sides of a contact area, making tighter butting, avoiding accidental opening of the cover, further enhancing the closing effect, and enhancing the user experience.

In this embodiment, the inner housing 150 is further provided with a power supply positioning shell 157; and the power supply positioning shell 157 is fixedly connected to the storage shell 151; and the power supply positioning shell 157 is configured to position and fix the rechargeable power supply 130. By the arrangement of the above structure, during use, the rechargeable power supply 130 is fixed by the power supply positioning shell 157, so that the rechargeable power supply is less likely to shake relative to the inner housing 150, thereby reducing the possibility of relative friction between the rechargeable power supply 130 and the inner housing 150, and further prolonging the service life of the inner housing 150.

In this embodiment, the inner housing 150 is further provided with a first mounting part 158; the outer housing 160 is provided with a second mounting part 161; and the first mounting part 158 is detachably connected to the second mounting part 161. By the arrangement of the above structure, during use, it is more convenient for connection and separation between the inner housing 150 and the outer housing 160. When the outer housing 160 that is easily damaged is damaged, it is convenient to replace the outer housing 160, instead of replacing the entire product, thereby the maintenance cost of a user for continuous use of this product.

In this embodiment, the first mounting part 158 is provided with a convex positioning strip 1581; the second mounting part 161 is provided with a positioning groove 1611; and when the first mounting part 158 is connected to the second mounting part 161, the convex positioning strip 1581 cooperates with the positioning groove 1611 for positioning to avoid misalignment during the connection between the inner housing 150 and the outer housing 160. The first mounting part 158 is provided with a convex clamping strip 1582; the second mounting part 161 is provided with a convex clamping block 1612; and when the first mounting part 158 is connected to the second mounting part 161, the convex clamping strip 1582 is matched and clamped with the convex clamping block 1612, so that the inner housing 150 and the outer housing 160 are connected by clamping. By the arrangement of the above structure, during use, the positioning is more accurate when the inner housing 150 and the outer housing 160 are connected. It is less likely to have a positioning deviation during mounting, which further lowers the mounting difficulty and enhances the user experience.

In this embodiment, the convex positioning strip 1581 is arranged around the convex clamping strip 1582 in a spacing manner; the convex clamping strip 1582 is provided with a clamping strip hole 1583; and a position of the clamping strip hole is correspondingly spaced apart from the convex positioning strip 1581. The positioning groove 1611 is continuously provided around the convex clamping block 1612; and a position of the convex clamping block 1612 is matched with the position of the clamping strip hole 1583. By the arrangement of the above structure, during use, the clamping between the inner housing 150 and the outer housing 160 is more stable. It is less likely to have looseness after mounting, which further lowers the mounting difficulty and enhances the user experience.

In this embodiment, the target hand warmer 300 is a hand warmer assembly. The storage shell 151 is provided with a clamping protrusion 1511 matched with the hand warmer assembly. The clamping protrusion 1511 enables the storage shell 151 to lock the hand warmer assembly. By the arrangement of the above structure, during use, the clamping protrusion 1511 in the storage shell 151 can restrain the shaking of the target hand warmer 300 in the accommodating space 120 and stably lock the target hand warmer 300, thereby reducing the friction frequency between the target hand warmer 300 and the storage shell 151, prolonging the service life of the product, and further enhancing the user experience.

In this embodiment, the hand warmer assembly includes two hand warmer units; and the two hand warmer units may be connected by magnetic suction or a buckle, or may be integrally formed.

In this embodiment, the circuit board 140 is provided with a charging circuit matched with the rechargeable power supply 130 and a charging port 141 connected to an external power supply. By the arrangement of the above structure, during use, the circuit board 140 is provided with the charging circuit matched with the rechargeable power supply 130, which can improve the charging efficiency of the rechargeable power supply 130 and further enhance the user experience.

In this embodiment, the circuit board 140 is provided with a discharging circuit and a discharging port 142 which are matched with the target hand warmer 300. By the arrangement of the above structure, during use, the circuit board 140 is provided with the discharging circuit and the discharging port 142 which are matched with the target hand warmer 300, which can improve the charging efficiency of the rechargeable power supply 130 for the power bank hand warmer, and further enhance the user experience.

One or more implementation modes are provided above in combination with specific contents, and it is not deemed that the specific implementation of the present disclosure is limited to these specifications. Any technical deductions or replacements approximate or similar to the method and structure of the present disclosure or made under the concept of the present disclosure shall fall within the scope of protection of the present disclosure.

The invention claimed is:

1. A hand warmer charging case, comprising:
an accommodating housing, wherein the accommodating housing is provided with a storage space for storing a target power bank hand warmer; the accommodating housing is further provided with an accommodating space; the accommodating space is configured to accommodate a rechargeable power supply and a circuit board matched with the rechargeable power supply, wherein the accommodating housing comprises an inner housing and an outer housing coupled with the inner housing, the storage space is provided in the inner housing, and the accommodating space is defined between the outer housing and the inner housing, and when the target power bank hand warmer is placed in the storage space, the rechargeable power supply charges the target power bank hand warmer; and
an accommodating cover, wherein the accommodating cover is movably connected to the accommodating housing in a movable manner, and is configured to close or open the storage space.

2. The hand warmer charging case according to claim 1, wherein the inner housing is provided with a storage shell for defining the storage space; the storage shell is provided with a storage opening communicated to the storage space; the accommodating cover comprises an inner cover and an outer cover; the inner cover is provided with a storage chamber and an opening communicated to the storage chamber; and the opening corresponds to the storage opening.

3. The hand warmer charging case according to claim 2, wherein the inner housing is provided with a positioning boss; the positioning boss is in a similarly trapezoid shape with a narrow top and a wide bottom; the inner cover is provided with a positioning chamber and a positioning opening communicated to the positioning chamber; and the positioning opening corresponds to the positioning boss.

4. The hand warmer charging case according to claim 2, further comprising a connecting shaft, wherein the accommodating housing and the accommodating cover are movably connected through the connecting shaft to enable the accommodating cover to close or open the storage space.

5. The hand warmer charging case according to claim 4, wherein the inner housing is provided with a connecting boss; the outer cover is provided with a connecting groove corresponding to the connecting boss; and the connecting boss and the connecting groove are movably connected through the connecting shaft.

6. The hand warmer charging case according to claim 5, wherein the connecting boss is provided with a connecting hole; connecting clamping slots are provided in two ends of the connecting groove; the connecting shaft passes through the connecting hole of the connecting boss and is clamped with the connecting clamping slots provided in the two ends of the connecting groove.

7. The hand warmer charging case according to claim 2, wherein the inner housing is provided with a first butting part; the inner cover is provided with a second butting part; and when the accommodating cover closes the storage space, the first butting part is butted to the second butting part.

8. The hand warmer charging case according to claim 7, wherein a first magnetic suction element is arranged below the first butting part, and a second magnetic suction element is arranged above the second butting part; and when the first butting part is butted to the second butting part, attraction force exists between the first magnetic suction element and the second magnetic suction element.

9. The hand warmer charging case according to claim 2, wherein the inner housing is further provided with a power supply positioning shell; and the power supply positioning shell is fixedly connected to the storage shell; and the power supply positioning shell is configured to position and fix the rechargeable power supply.

10. The hand warmer charging case according to claim 2, wherein the inner housing is further provided with a first mounting part; the outer housing is provided with a second mounting part; and the first mounting part is detachably connected to the second mounting part.

11. The hand warmer charging case according to claim 10, wherein the first mounting part is provided with a convex positioning strip; the second mounting part is provided with a positioning groove; and when the first mounting part is connected to the second mounting part, the convex positioning strip cooperates with the positioning groove for positioning to avoid misalignment during the connection between the inner housing and the outer housing.

12. The hand warmer charging case according to claim 11, wherein the first mounting part is provided with a convex clamping strip; the second mounting part is provided with a convex clamping block; and when the first mounting part is connected to the second mounting part, the convex clamping strip is matched and clamped with the convex clamping block, so that the inner housing and the outer housing are connected by clamping.

13. The hand warmer charging case according to claim 12, wherein the convex positioning strip is arranged around the convex clamping strip in a spacing manner; the convex clamping strip is provided with a clamping strip hole; and a position of the clamping strip hole is correspondingly spaced apart from the convex positioning strip.

14. The hand warmer charging case according to claim 13, wherein the positioning groove is continuously provided around the convex clamping block; and a position of the convex clamping block is matched with the position of the clamping strip hole.

15. The hand warmer charging case according to claim 2, wherein the storage shell is provided with a clamping protrusion matched with the target power bank hand warmer; and the clamping protrusion enables the storage shell to lock the target power bank hand warmer, and the target power bank power bank hand warmer is a hand warmer assembly comprising one power bank hand warmer or two power bank hand warmers connected by magnetic suction or a buckle.

16. The hand warmer charging case according to claim 1, wherein the circuit board is provided with a discharging circuit and a discharging port which are matched with the target power bank hand warmer, and the circuit board is provided with a charging circuit matched with the rechargeable power supply and a charging port connected to an external power supply.

17. A hand warmer kit, comprising:
at least one power bank hand warmer;
an accommodating housing, wherein the accommodating housing is provided with a storage space for storing the at least one power bank hand warmer; the accommodating housing is further provided with an accommodating space; the accommodating space is configured to accommodate a rechargeable power supply and a circuit board matched with the rechargeable power supply, wherein the circuit board is provided with a discharging circuit therein and a discharging port which are matched with the at least one power bank hand warmer, and when the at least one power bank hand warmer is placed in the storage space, the rechargeable power supply directly charges the at least one power bank hand warmer; and
an accommodating cover, wherein the accommodating cover is movably connected to the accommodating housing in a movable manner, and is configured to close or open the storage space.

18. The hand warmer kit according to claim 17, wherein the accommodating housing comprises an inner housing and an outer housing coupled with the inner housing, the storage space is provided in the inner housing, and the accommodating space is defined between the outer housing and the inner housing.

19. The hand warmer kit according to claim 18, wherein the inner housing is further provided with a power supply positioning shell, and the power supply positioning shell is configured to position and fix the rechargeable power supply.

* * * * *